US010022467B2

(12) United States Patent
Chang

(10) Patent No.: US 10,022,467 B2
(45) Date of Patent: Jul. 17, 2018

(54) TRASHCAN

(71) Applicants: Magikan Inc., Chungcheongnam-do (KR); Janibell, Inc., Rancho Cucamonga, CA (US)

(72) Inventor: Kwang Ok Chang, Gyeonggi-do (KR)

(73) Assignee: Magikan Inc., Chungcheongnam-do (KR)

( * ) Notice: Subject to any disclaimer, the term of this patent is extended or adjusted under 35 U.S.C. 154(b) by 44 days.

(21) Appl. No.: 15/334,872

(22) Filed: Oct. 26, 2016

(65) Prior Publication Data

US 2018/0110893 A1    Apr. 26, 2018

(51) Int. Cl.
*B65F 1/16* (2006.01)
*A61L 11/00* (2006.01)
*B65F 1/06* (2006.01)
*A61L 2/10* (2006.01)
(Continued)

(52) U.S. Cl.
CPC ................ *A61L 11/00* (2013.01); *A61L 2/10* (2013.01); *A61L 2/202* (2013.01); *A61L 9/12* (2013.01); *B65F 1/062* (2013.01); *B65F 1/1638* (2013.01); *B65F 1/1646* (2013.01); *A61L 2202/11* (2013.01); *A61L 2202/14* (2013.01);
(Continued)

(58) Field of Classification Search
CPC ........... A47G 19/32; A47G 29/00; H02P 9/18; G05B 2219/37604; B65F 1/163; B65F 1/062; B65F 1/1623; B65F 1/1646; B65F 43/38
See application file for complete search history.

(56) References Cited

U.S. PATENT DOCUMENTS 8,776,278 B1* 7/2014 Dorra .................... A47K 13/302
4/233
2005/0258794 A1* 11/2005 Fukuizumi ............. B64D 11/02
318/480
(Continued)

FOREIGN PATENT DOCUMENTS

JP         2005-335822      12/2005
JP         3146752          11/2008
JP         3146752 U    *  11/2008
(Continued)

OTHER PUBLICATIONS

KR Office Action of Corresponding Appln. No. 10-2015-0112966.

*Primary Examiner* — Bickey Dhakal
(74) *Attorney, Agent, or Firm* — Berenato & White, LLC

(57) ABSTRACT

A trashcan automatically opens and closes a trashcan lid and prevents offensive odor due to UV (ultraviolet) disinfection. The trashcan includes a case whose upper face is openable; a lid coupled to the case to be opened and closed and to seal the trashcan, and a sterilizer on the lid generating ultraviolet rays and ozone toward the trashcan for sterilization and deodorization. An opening and closing unit automatically opens and closes the lid by sensing user access. A microcomputer controls operation of the UV sterilization lamp at regular intervals when the lid is closed and the opening and closing unit. Accordingly, it is possible to prevent offensive odor from being caused by sterilizing and deodorizing the inside of the trashcan, and it is convenient for users to discard waste or dirt into the trashcan by automatically opening the trashcan lid for a certain time according to the user access.

18 Claims, 7 Drawing Sheets

(51) Int. Cl.
*A61L 2/20* (2006.01)
*A61L 9/12* (2006.01)

(52) U.S. Cl.
CPC .... *A61L 2209/111* (2013.01); *B65F 2210/129* (2013.01); *B65F 2210/168* (2013.01)

(56) References Cited

U.S. PATENT DOCUMENTS

2007/0182551 A1* 8/2007 Yang .................. B65F 1/08
 340/545.3
2011/0020184 A1* 1/2011 Sun .................... A61L 2/10
 422/114

FOREIGN PATENT DOCUMENTS

| | | |
|---|---|---|
| KR | 20-0362238 | 9/2004 |
| KR | 200362238 Y1 * | 9/2004 |
| KR | 10-2013-0002971 | 1/2013 |

* cited by examiner

TRASHCAN

FIELD OF THE INVENTION

The present invention relates to a trashcan, and in particular, to a trashcan capable of automatically opening and closing a trashcan lid and preventing offensive odor due to UV (ultraviolet) disinfection, to thereby achieve convenience in use and environmental hygiene.

BACKGROUND OF THE INVENTION

In general, trashcans are used in many places such as homes and offices as well as dining rooms and bathrooms, as commodity items that collect dirt and garbage generated in human lives.

In recent years, social attention and care to waste separation processing increases with social craze called a "volume-rate garbage disposal system". In addition, trashcans play functional roles for waste separate collection and a role in interior decoration for living space.

Such trashcans are formed to have a trashcan lid at a trashcan entrance to suppress offensive odor from being generated from waste or to have various collection features to easily collect and discard waste separately.

In addition, trashcans are formed to have a clean and beautiful design, and are used as a tool to enrich human lives at one corner of living spaces.

Trashcans in accordance with the prior art are formed in a container shape that can hold a certain amount of waste, and have a lid that blocks an upper opening that can be opened and closed.

In recent years, trashcans are provided to have a built-in roll of a plastic bag so as to achieve an easy collection of waste as well as a hygienic process for the collected waste.

In other words, a roll of a plastic bag is provided inside a trashcan, to thus allow waste to be processed once at a time. Accordingly, dirt is not left on the inside of the trashcan, to thereby hygienically achieve treatment of dirt and the management of trashcans.

However, most of the traditional trashcans containing a traditional built-in roll of a plastic bag have the following defects:

First, the offensive odor is caused by the dirt stored inside the trashcan, and thus a lid is laid on top of the trashcan in order to prevent this, but the offensive odor is leaked out of a gap between the lid and the trashcan.

Second, in order to open and close the lid of the trashcan, users must open and close the lid of the trashcan directly by hand, or tread on a pedal to open and close the lid by an interlocking action of the lid and the pedal.

In other words, although providing a trashcan lid to prevent the offensive odor, the offensive odor still occurs, to thus cause unhygienic environments and weight rather inconveniences for opening and closing the lid.

SUMMARY OF THE INVENTION

Accordingly, it is an object of the present invention to provide a trashcan capable of automatically opening and closing a trashcan lid and preventing offensive odor due to UV (ultraviolet) disinfection, to thereby achieve convenience in use and environmental hygiene.

To achieve the above object of the present invention, there is provided a trashcan comprising: a case whose upper face is opened; a lid coupled on top of the case to be opened and closed and to seal the trashcan; a sterilizer provided on the lid, and generating ultraviolet rays and ozone toward an inner space of the trashcan for sterilization and deodorization; an opening and closing unit for automatically opening and closing the lid by sensing a user access; a power supply unit for supplying power for operation of the sterilizer and the opening and closing unit; and a microcomputer for controlling operations of the sterilizer and the opening and closing unit, wherein the opening and closing unit comprises: a proximity sensor that is installed on the case surrounding the lid to detect a user access; and a driving unit that opens and closes the lid according to the detection of the proximity sensor, wherein the driving unit comprises: a motor; a driver that drives the motor; a vertical bar that is provided between one side of the motor and a hinge side of the lid, and that is rotated according to rotation of the motor; and a resilient member that is provided at the other side of the motor and constrains the rotation of the motor, to thus facilitate position restoration.

DETAILED DESCRIPTION OF THE PREFERRED EMBODIMENT(S)

Hereinafter, a preferred embodiment of the present invention will be described with reference to the accompanying drawings.

Figure 1:
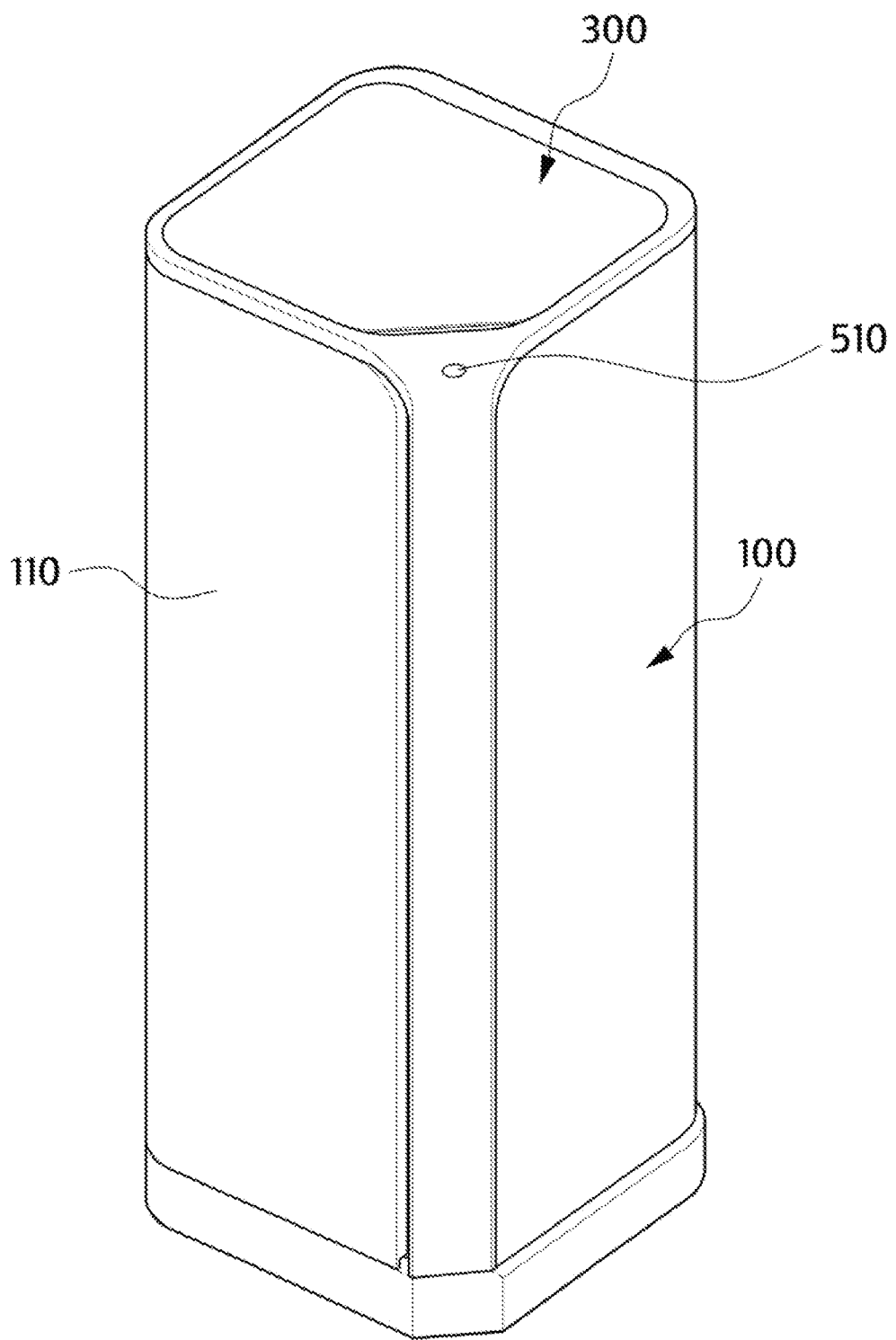
FIGS. 1 and 2 are perspective views showing the front and back exterior appearance of a trashcan according to an embodiment of the present invention.
Figure 2:
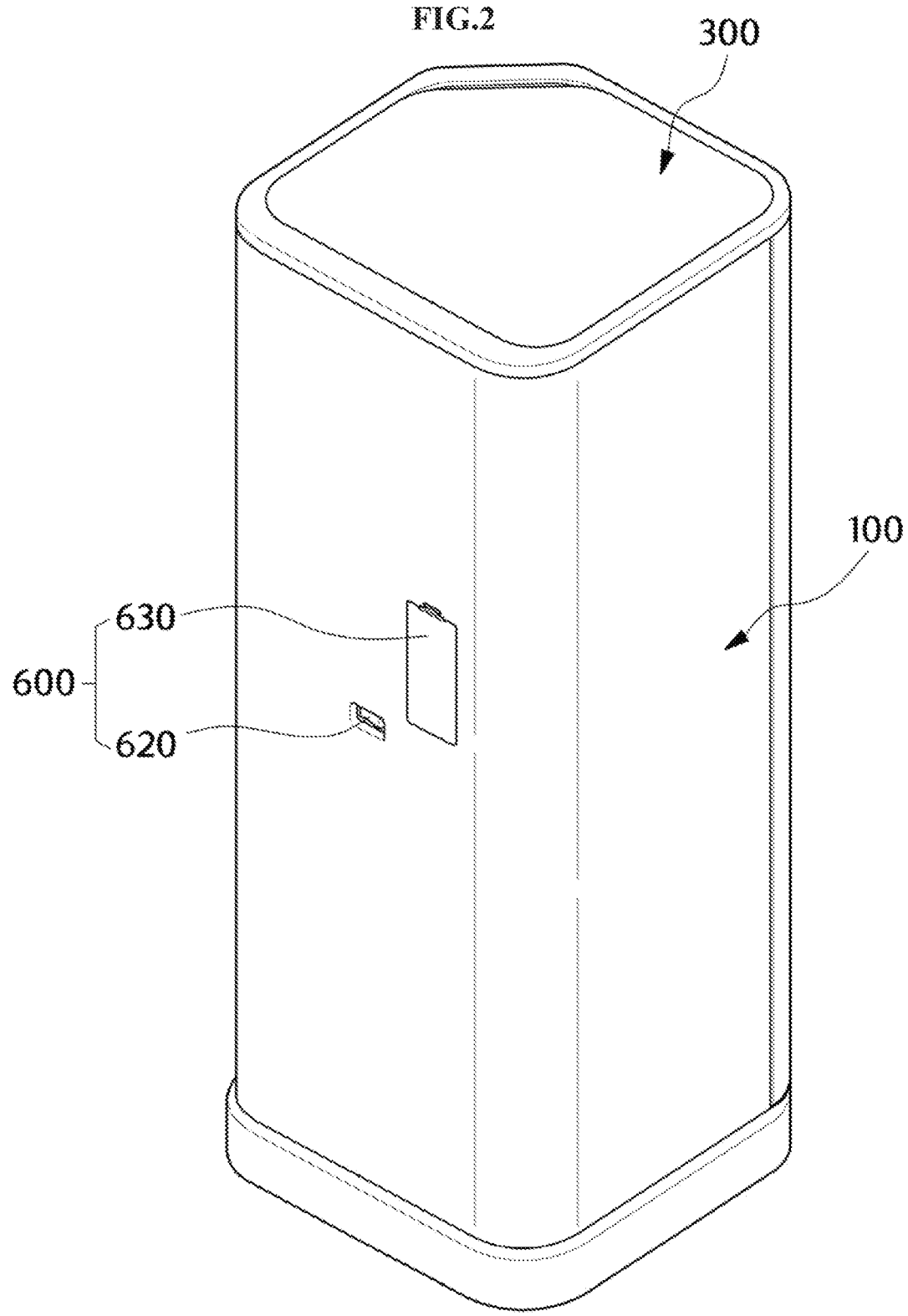
Figure 3:
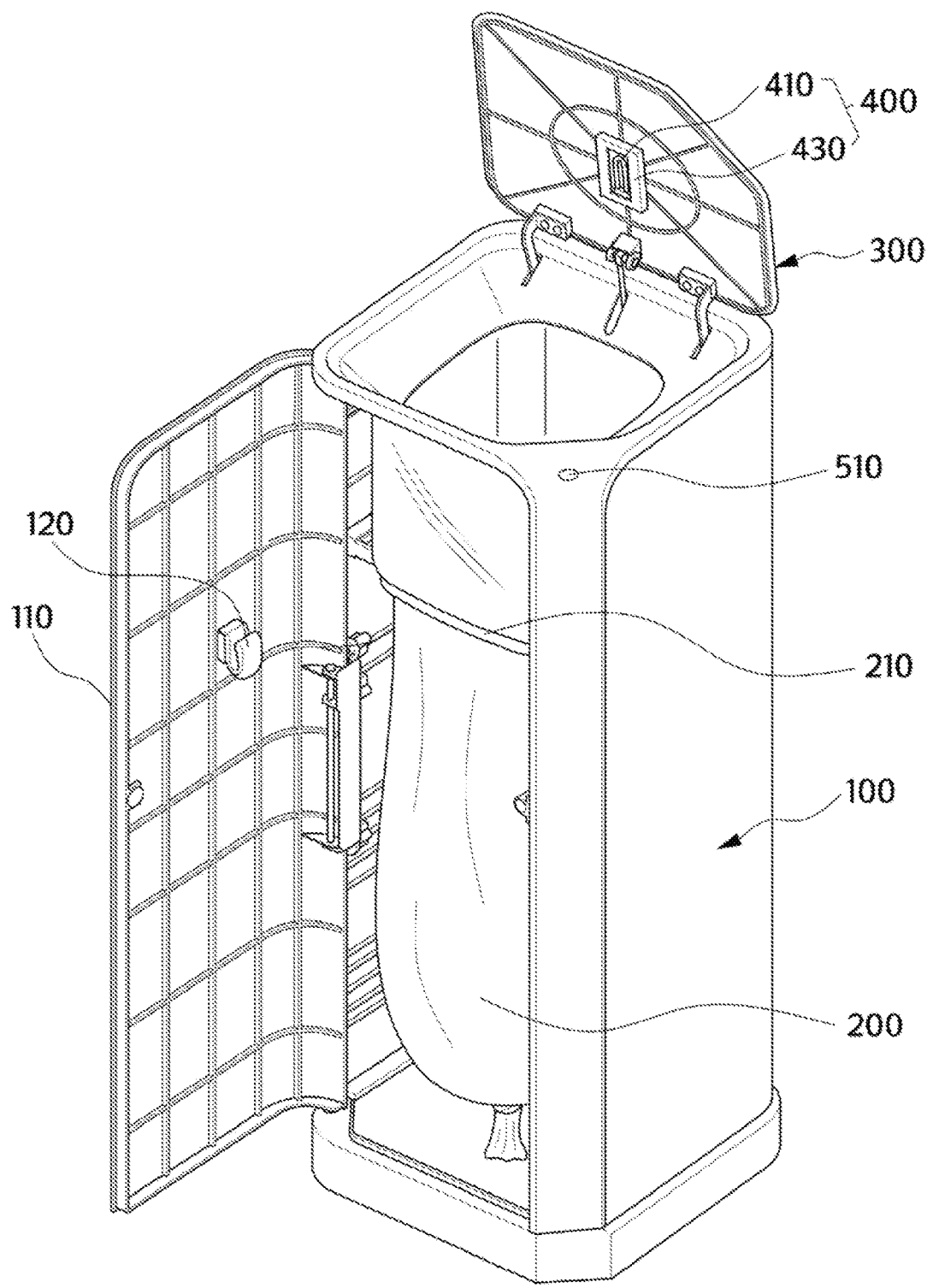
FIG. 3 is a perspective view showing a door and a lid that are opened, in a trashcan in accordance with an embodiment of the present invention.
Figure 4:
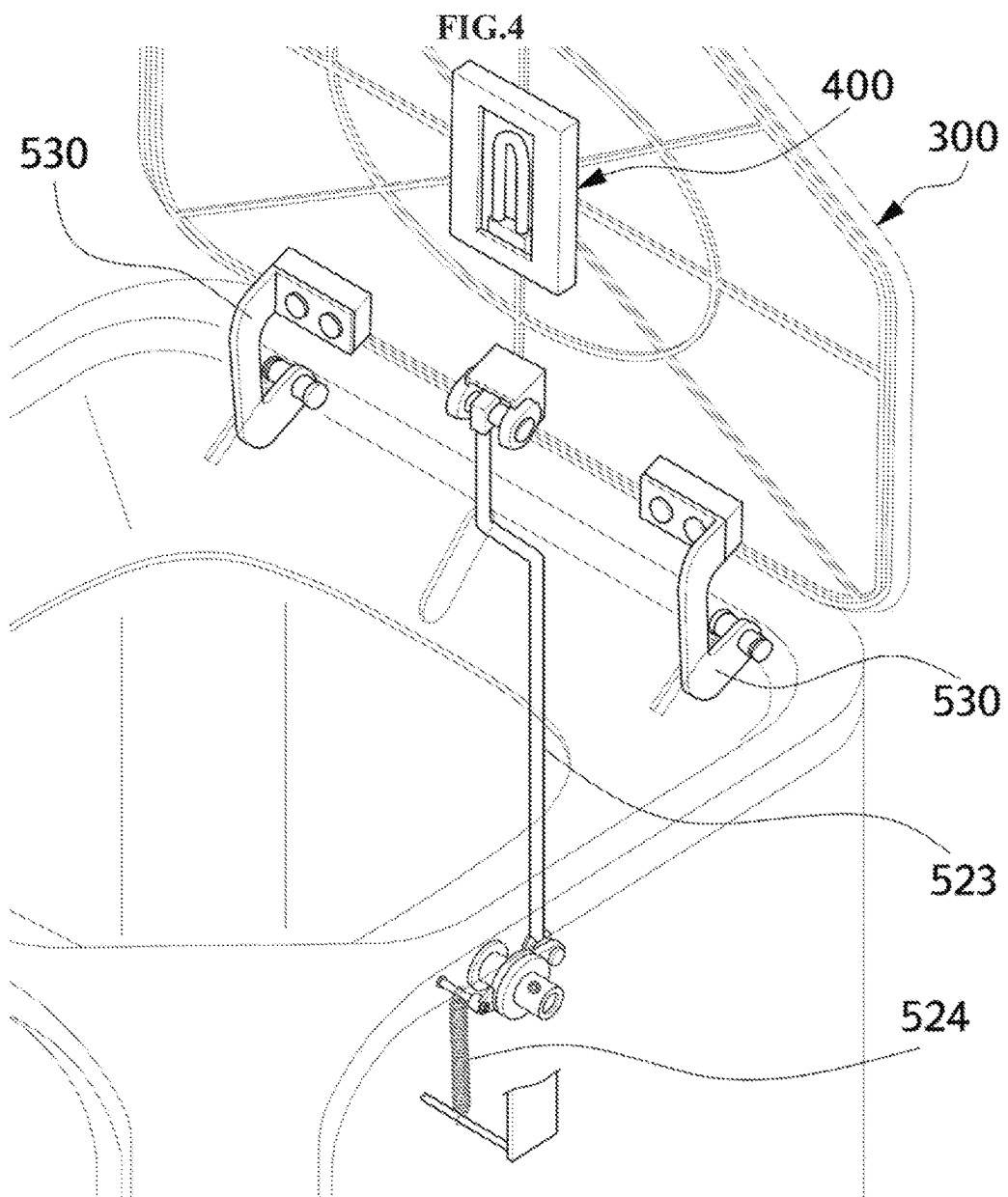
FIGS. 4 to 6 are views for functionally explaining an opening and closing action of the trashcan lid in accordance with an embodiment of the present invention.
Figure 5:
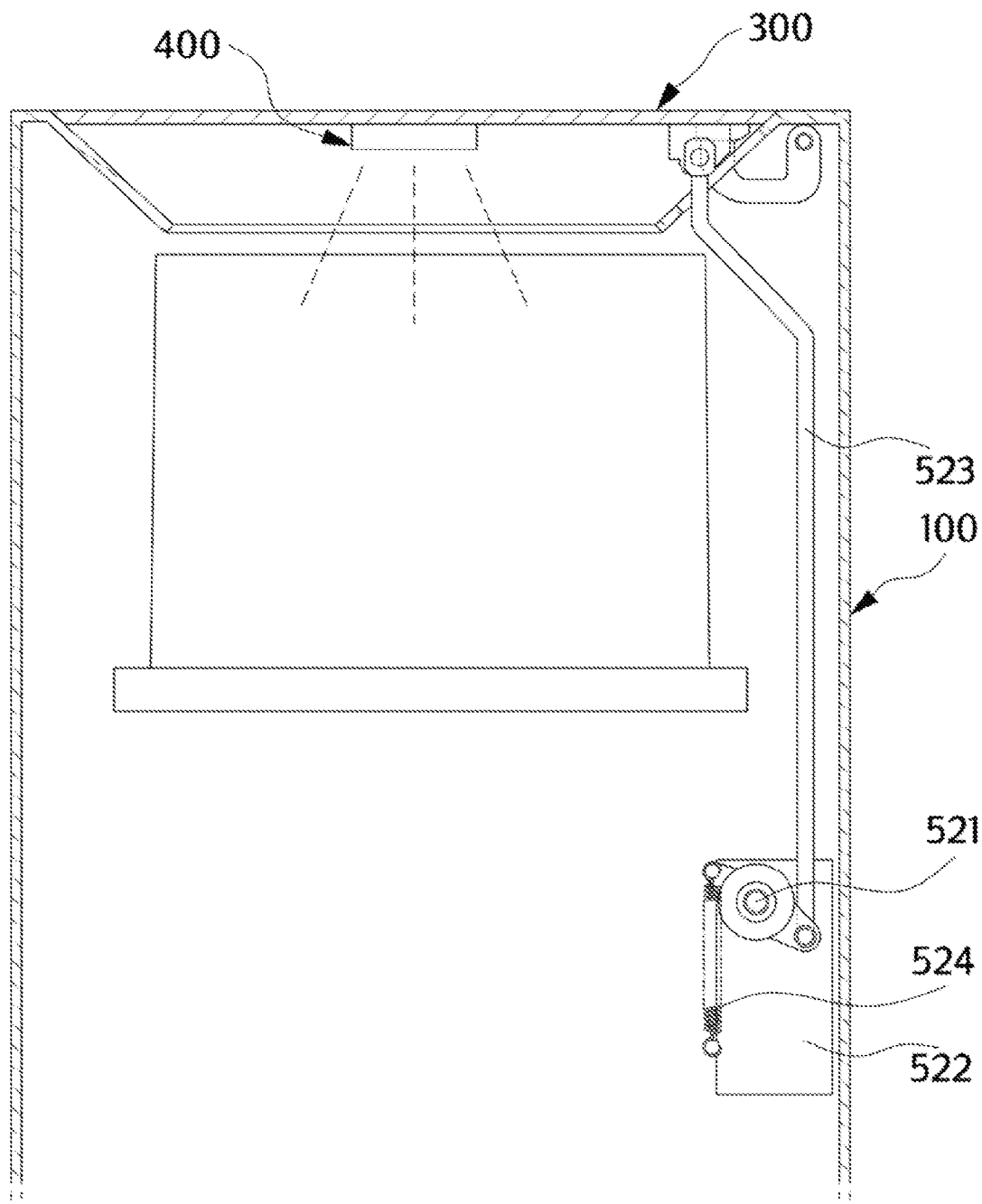
Figure 6:
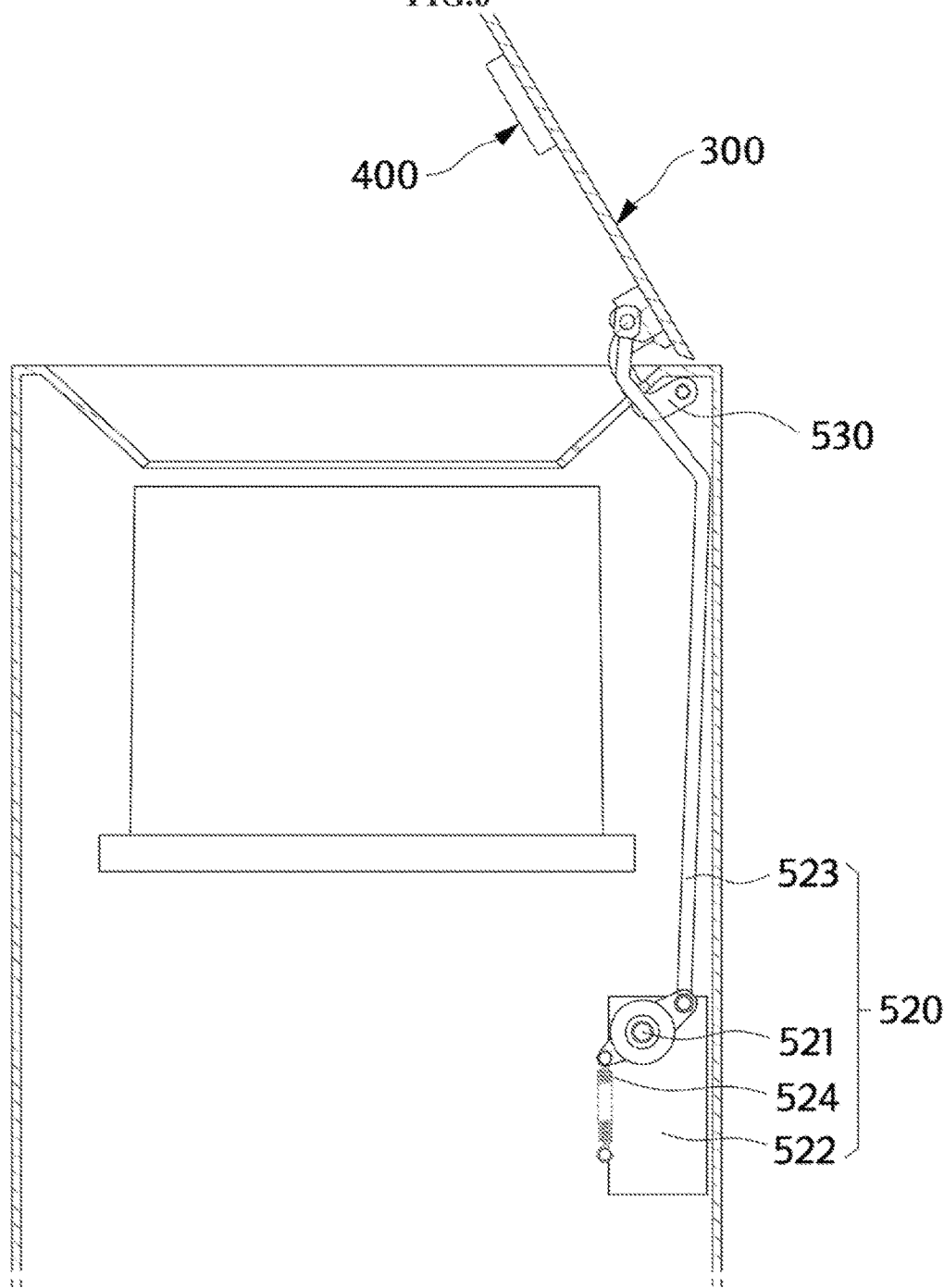
Figure 7:
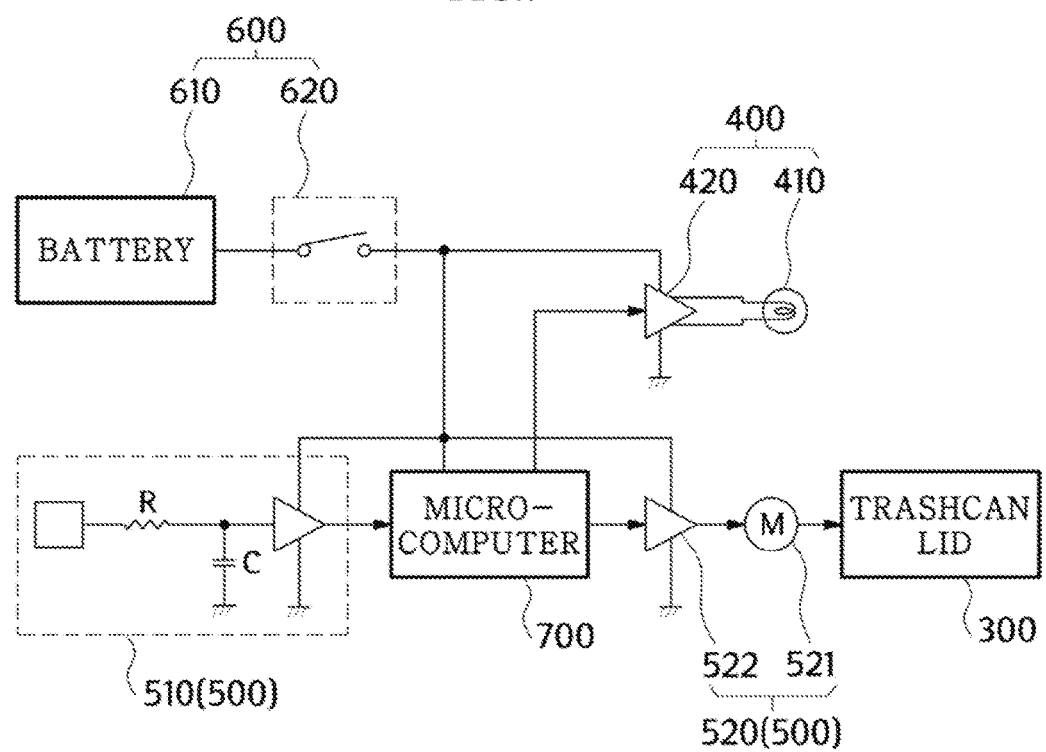
FIG. 7 is a block diagram showing a trashcan according to an embodiment of the present invention.

FIGS. 1 and 2 show the front and back exterior appearance of a trashcan according to an embodiment of the present invention. FIG. 3 shows a door and a lid that are opened, in a trashcan in accordance with an embodiment of the present invention. FIGS. 4 to 6 are views for functionally explaining an opening and closing action of the trashcan lid in accordance with an embodiment of the present invention. FIG. 7 shows a trashcan according to an embodiment of the present invention.

With reference to FIGS. 1 to 7, a trashcan according to an embodiment of the present invention includes: a case 100 that is provided with a roll of a plastic bag 200 therein; and a lid 300 for opening and closing an upper portion of the case 100.

The trashcan according to the embodiment of the present invention includes: a sterilizer 400 generating ultraviolet rays and ozone toward an inner space of the case 100; an opening and closing unit 500 for automatically opening and closing the lid 300 by sensing a user access to the trashcan; a power supply unit 600 for supplying operational power to electrical components; and a microcomputer 700 for controlling overall operations of the trashcan for automatic opening and closing and ultraviolet sterilization.

As shown in FIGS. 1 to 3, the case 100 constitutes the overall appearance of the trashcan, and is formed with a predetermined area in the inside of which a roll of a plastic bag 200 is installed.

In addition, a door 110 is installed in front of the case 100.

In this embodiment, it is preferable for the convenience of a user manipulation that the door 110 should be configured in a push-type locking structure to be opened and closed by a press operation of a push-button.

The door 110 opens and closes an inside of the case 100, and a roll of the plastic bag 200 in which the dirt has been collected is discharged through the door 110.

In addition, a cutter 120 is installed at one side in the inside of the case 100.

The cutter 120 acts to cut part of the roll of the plastic bag 200, and it is preferable for the safety that the cutter 120 should be installed in the inner side of the door 110.

Then, the roll of the plastic bag 200 is a part of garbage collection and is installed in the case 100.

The roll of the plastic bag 200 is provided in a roll form, and is installed in a roll plastic frame 210 so as to be continuously supplied downwards.

Here, the roll of the plastic bag 200 is opened by the roll plastic frame 210 so that the inner portion of the roll of the plastic bag 200 is widely open.

Then, the lid 300 is provided on top of an upper portion of the case 100 to thus open and close the case 100.

Further, a sterilizer 400 is installed on an inner surface of the lid 300.

The sterilizer 400 includes: an ultraviolet (UV) sterilization lamp 410 which generates ozone by irradiating ultraviolet rays toward an inside surface of the case 100; and a converter 420 for controlling a radiation intensity of the UV sterilization lamp 410.

Here, a reflector 430 is configured on an outer surface of the ultraviolet sterilization lamp 410 to allow ultraviolet rays to be irradiated inward the roll of the plastic bag 200 installed on the case 100.

The opening and closing unit 500 includes: a proximity sensor 510 that detects a user access; and a driving unit 520 that automatically opens and closes the lid 300 according to the detection of the user access of the proximity sensor 510.

The proximity sensor 510 is preferably installed at a predetermined position around the lid 300 for a sensing accuracy.

As shown in FIGS. 4 to 7, the driving unit 520 is configured by including a motor 521 and a driver 522 for driving the motor 521.

In addition, the driving unit 520 further includes: a vertical bar 523 that is provided between one side of the motor 521 and a hinge side of the lid 300, and that is rotated according to rotation of the motor; and a resilient member 524 that is provided at the other side of the motor 521 and constrains the excessive rotation of the motor, to thus facilitate position restoration.

Meanwhile, the opening and closing unit 500 is configured to include a movable body 530 which is interlocked between the case 100 and the lid 300 in association with rotation of the vertical bar 523 of the driving unit 520, in which the movable body 530 is installed at both sides around the vertical bar 523.

The power supply unit 600 is configured by including a battery 610 and a power switch 620.

In this embodiment, the power switch 620 is installed as shown in FIG. 2.

In addition, a battery case 630 is installed on a rear surface of the case 100, so that the battery 610 can be easily inserted into the battery case 630 and the battery 610 can be easily detached from the battery case 630 from the outside.

The trashcan configured as described in accordance with the embodiment of the present invention will perform the following action.

First, a user turns on the power switch 620 installed on the rear surface of the case 100 to allow power of the battery 610 to be supplied to electric components of the trashcan to enable the operation of the trashcan.

The microcomputer 700 controls the operation of the opening and closing unit 500 so that the lid 300 of the trashcan is opened and then closed automatically initially when the power switch 620 is turned on, to thus inform a user that the trashcan is in a normal operational state.

Since then, the microcomputer 700 controls the lid 300 to be opened and closed when a user's approach is sensed.

That is, when a user gains access to the trashcan, the proximity sensor 510 installed at a predetermined position of the case 100 detects the user's access and then transfers the sensed signal to the microcomputer 700.

The proximity sensor 510 is a capacitance capacitor type sensor and detects changes of a capacitance value due to a user access within a certain distance.

When the microcomputer 700 compares the detected signal with a reference signal to then be determined as a user access in the comparison result, the microcomputer 700 operates the driving unit 520 of the opening and closing unit 500 to thereby control the lid 300 to be opened automatically for a set time and then closed.

As shown in FIGS. 5 and 6, the driver 522 of the driving unit 520 drives the motor 521 in accordance with the control of the microcomputer 700, so that the driving force of the motor 521 is transmitted to the vertical bar 523, to thereby push or pull one side of the lid 300 and thus open and close the lid 300 about a hinge of the lid 300. In this case, the movable body 530 provided at both sides of the vertical bar 523 is also interlocked with the vertical bar 523 to thereby push or pull the lid 300 and thus aid opening and closing of the lid 300.

After lapse of a predetermined set time, the microcomputer 700 controls driving of the driver 522 to thereby stop the rotation of the motor 521, and thus the vertical bar 523 is lowered gradually by a resilient member 524 to thus allow the lid 300 to cover an upper portion of the case 100 around the hinge of the lid 300.

Therefore, although the trashcan lid 300 is not opened and closed by hand, just a user access makes the trashcan lid 300 automatically opened and then is automatically closed after a predetermined time has elapsed, to thus achieve convenience in use.

Meanwhile, the microcomputer 700 operates the UV sterilization lamp 410 at regular intervals in the state where the lid 300 is closed, to thereby irradiate the inside of the trashcan with ultraviolet rays to sterilize bacteria and thus remove the odor.

UV rays are about 2% of the total sun light, and make the beneficial actions such as a bactericidal action and a synthesis of vitamin D in the skin. As a phenomenon commonly found in our everyday lives around, irradiating the laundry, dishes, bedding, etc., with the sun light is because the sun is subject to the solar sterilization. The deoxyribonucleic acids (DNAs) in the cells are changed by ultraviolet irradiation, and a proliferative capacity of bacteria is lost due to a failure in metabolism. This is referred to as sterilization.

In particular, UV rays generate ozone ($O_2$) at 200 nm or below, and exhibit optimum sterilization and deodorization effects at around 184.9 nm.

Accordingly, the radiation intensity of the ultraviolet sterilization lamp 410 is controlled and used at the best condition via the converter 420.

When waste is put into the trashcan according to the embodiment of the present invention, UV sterilization lamp 410 irradiates ultraviolet rays to generate ozone before the offensive odor is generated in every predetermined time to thus continue sterilization.

When the lid 300 is opened by a user access, the microcomputer 700 automatically turns off the ultraviolet sterilization lamp 410, so as not to irradiate the ultraviolet light or ozone to the human body.

Thus, the trashcan according to the embodiment of the present invention can be used in a sanitary manner by carrying out sterilization to avoid the offensive odor.

The trashcan according to the embodiment of the present invention is provided with a UV sterilization lamp on the inside surface of the lid so as to be capable of sterilizing and deodorizing the inner portion of the trashcan, to thereby have an effect of preventing offensive odor from being generated by the waste stored inside a garbage bag.

The trashcan according to the embodiment of the present invention operates the proximity sensor when a user comes close to the trashcan and automatically opens the lid of the trashcan, to then automatically close the lid after a predetermined time has elapsed, to thereby provide an effect of making it much more convenient to put waste into the trashcan.

As described above, it will be appreciated that the technical structure of the present invention described above can be embodied in other specific forms without changing the technical spirit or essential features by those skilled in the art.

As described above, the present invention has been described with respect to particularly preferred embodiments. However, the present invention is not limited to the above embodiments, and it is possible for one who has an ordinary skill in the art to make various modifications and variations, without departing off the spirit of the present invention. Thus, the protective scope of the present invention is not defined within the detailed description thereof but is defined by the claims to be described later and the technical spirit of the present invention.

What is claimed is:

1. A trashcan comprising:
a case comprising an upper face that is open;
a lid coupled on top of the case to be opened and closed and to seal the trashcan;
a sterilizer provided on the lid, and configured to generate ultraviolet rays and ozone toward an inner space of the trashcan for sterilization and deodorization;
an opening and closing unit installed at the case close to the lid;
a power supply unit for supplying power for operation of the sterilizer and the opening and closing unit; and
a microcomputer for controlling operations of the sterilizer and the opening and closing unit,
wherein the opening and closing unit comprises:
a proximity sensor that is installed on the case surrounding the lid to detect a user access; and
a driving unit that automatically opens and closes the lid according to the detection of the user access by the proximity sensor,
wherein the driving unit comprises:
a motor;
a driver that drives the motor;
a vertical bar that is provided between one side of the motor and a hinge side of the lid, and that is rotated according to rotation of the motor; and
a resilient member that is provided at the other side of the motor and constrains the rotation of the motor, to thus facilitate position restoration; and
wherein the microcomputer is operable: to control the lid to be opened and then closed automatically when power is initially supplied to the trashcan, and to thus inform a user that the trashcan is in a normal operational state; to drive the driving unit according to detection of the proximity sensor, to thus control the lid to be opened and then closed for a preset time; and to operate the sterilizer at regular intervals in a state where the lid is closed.

2. The trashcan of claim 1, wherein the sterilizer comprises:
an ultraviolet (UV) sterilization lamp which is installed on an inside surface of the lid; and
a converter for controlling a radiation intensity of the UV sterilization lamp.

3. The trashcan of claim 2, wherein a radiation range of the UV sterilization lamp between 184.9 nm and 200 nm.

4. The trashcan of claim 2, further comprising reflector mounted on the rear of the UV sterilization lamp to irradiate ultraviolet rays generated from the UV sterilization lamp to the inner space of the case trashcan.

5. The trashcan of claim 1, further comprising first and second movable bodies installed between the case and the lid at both sides around the vertical bar to push or pull the lid in association with rotation of the vertical bar.

6. The trashcan of claim 1, wherein the opening and closing unit operates to allow the vertical bar to be gradually lowered by the resilient member and the lid to cover an upper portion of the case around a hinge of the lid, when the motor rotation is stopped under the control of the microcomputer.

7. The trashcan of claim 1, wherein the power supply unit comprises:
a power switch; and
a battery that is a power source.

8. The trashcan of claim 1, wherein the sterilizer is positioned to irradiate the ultraviolet rays downwardly into the case.

9. The trashcan of claim 1, wherein:
the motor is associated with the vertical bar to raise the vertical bar so that, the vertical bar pushes the lid open; and
the resilient member is associated with the vertical bar o lower the vertical bar so that the vertical bar pulls the lid closed.

10. A trashcan, comprising:
a case comprising an open upper face;
a lid coupled on top of the case and movable between opened and closed positions;
a sterilizer operable associated with the lid and configured to generate ultraviolet rays and ozone toward an inner space of the case;
an opening and closing unit;
a power supply unit comprising a power switch switchable into an on-state to supply power for operation of the sterilizer and the opening and closing unit; and a microcomputer for controlling operations of the sterilizer and the opening and closing unit,
wherein the opening and closing unit comprises:
a proximity sensor configured to detect a user attempting to access the inner space of the trashcan; and a driving unit configured to automatically" open and close the lid in response to detection of the user by" the proximity sensor, wherein the driving unit comprises: a motor;

a vertical bar that is provided between one side of the motor and a hinge side of the lid, and that is rotated in response to rotation of the motor; and a resilient member that is provided at the other side of the motor and configured to facilitate closing of the lid; and wherein the microcomputer is operable to control the driving unit to automatically open the lid when the power switch is initially turned to the on-state without requiring detection of the user by the proximity sensor, to thus inform the user that the trashcan is in a state of operation; and wherein the microcomputer is further operable to drive the driving unit according to detection of the proximity sensor and thus control the lid to be opened and then closed for a preset time, and to operate the sterilizer at regular intervals when the lid is closed.

11. The trashcan of claim 10, wherein the sterilizer comprises:
an ultraviolet (UV) sterilization lamp installed on an inside surface of the lid; and
a converter for controlling a radiation intensity of the UV sterilization lamp.

12. The trashcan of claim 11, wherein the UV sterilization lamp is operable in a radiation range between 184.9 nm and 200 nm.

13. The trashcan of claim 11, further comprising a reflector mounted on the rear of the UV sterilization lamp to irradiate ultraviolet rays generated from the UV sterilization lamp to the inner space of the case.

14. The trashcan of claim 10, further comprising first and second movable bodies installed between the case and the lid at both sides of the vertical bar to push or pull the lid in association with rotation of the vertical bar.

15. The trashcan of claim 10, wherein the microcomputer is operable to stop rotation of the motor, and wherein the resilient member is configured to lower the vertical bar and thereby close the lid when motor rotation is stopped under the control of the microcomputer.

16. The trashcan of claim 10, wherein the power supply unit further comprises a battery.

17. The trashcan of claim 10, wherein the sterilizer is positioned to irradiate the ultraviolet rays downwardly into the case.

18. The trashcan of claim 10, wherein:
the motor is associated with the vertical bar to raise the vertical bar so that the vertical bar pushes the lid open; and
the resilient member is associated with the vertical bar to lower the vertical bar so that the vertical bar pulls the lid closed.

* * * * *